(12) United States Patent
Pessin (10) Patent No.: US 7,875,006 B2
(45) Date of Patent: Jan. 25, 2011

(54) NEEDLE PROTECTION DEVICE FOR A SYRINGE AND AN INJECTION DEVICE COMPRISING A SYRINGE AND SAID PROTECTION DEVICE

(75) Inventor: Olivier Pessin, Grezieu la Varenne (FR)

(73) Assignee: SEDAT, Irigny (FR)

( * ) Notice: Subject to any disclaimer, the term of this patent is extended or adjusted under 35 U.S.C. 154(b) by 64 days.

(21) Appl. No.: 10/507,913

(22) PCT Filed: Mar. 6, 2003

(86) PCT No.: PCT/FR03/00722

§ 371 (c)(1), (2), (4) Date: Mar. 18, 2005

(87) PCT Pub. No.: WO03/077977

PCT Pub. Date: Sep. 25, 2003

(65) Prior Publication Data

US 2005/0165353 A1 Jul. 28, 2005

(30) Foreign Application Priority Data

Mar. 18, 2002 (FR) .................................. 02 03338

(51) Int. Cl.
*A61M 5/32* (2006.01)
(52) U.S. Cl. ....................... 604/192; 604/198
(58) Field of Classification Search ................. 604/110, 604/192–198, 263
See application file for complete search history.

(56) References Cited

U.S. PATENT DOCUMENTS

| | | |
|---|---|---|
| 5,346,480 A | 9/1994 | Hess et al. |
| 5,573,513 A | 11/1996 | Wozencroft |
| 6,033,386 A | 3/2000 | Novacek et al. |
| 6,547,764 B2 * | 4/2003 | Larsen et al. ............... 604/192 |
| 6,719,730 B2 * | 4/2004 | Jansen et al. ............... 604/192 |
| 2001/0031949 A1 | 10/2001 | Asbaghi |
| 2002/0193746 A1 * | 12/2002 | Chevallier .................. 604/197 |

FOREIGN PATENT DOCUMENTS

| | | |
|---|---|---|
| EP | 1 066 848 A2 | 1/2001 |
| WO | WO 99 17823 A1 | 4/1999 |

* cited by examiner

*Primary Examiner*—Kevin C Sirmons
*Assistant Examiner*—Deanna K Hall
(74) *Attorney, Agent, or Firm*—Sughrue Mion, PLLC (57) ABSTRACT

A needle-protection device (2) for a syringe (1) having a needle (6), a tubular body (4) and an injection plunger (8). The device includes: a needle protector (22); a protector support (20); a spring (24) which presses against the support (20) and the protector (22), the support and protector being movable relative to one another between a retracted protector position, in which the needle of the syringe is exposed and the spring is locked in compression, and a deployed protector position in which the needle is disposed inside the protector and the spring is at least partially decompressed; and a mechanism for unlocking the spring. When locked, the spring (24) exhibits a predetermined force which is greater than the push force required to move the plunger (8) along essentially all of the injection stroke thereof. The mechanism has a digital support flange (50) which (i) transmits to the spring a compression force, which is less than the predetermined force, as the plunger slides along the injection stroke, and (ii) transmits to the spring a compression force, which is greater than the predetermined force, when the plunger reaches the end of the injection stroke.

19 Claims, 6 Drawing Sheets

FIG.11

NEEDLE PROTECTION DEVICE FOR A SYRINGE AND AN INJECTION DEVICE COMPRISING A SYRINGE AND SAID PROTECTION DEVICE

BACKGROUND OF THE INVENTION

The present invention relates to a needle protection device for a syringe which comprises a needle, a tubular body, to the distal end of which the needle is fixed, and an injection piston which is slidingly arranged in the body, this device comprising a needle protector which is substantially coaxial with the body of the syringe; a protector support which is fixedly joined to the body or which is provided with means for being fixedly joined to the body; a spring which is arranged between and in contact with the support and the protector, the support and the protector being movable relative to each other between a retracted position of the protector, in which the needle of the syringe is disengaged and the spring is locked in a compressed state, and a deployed position of the protector, in which the needle is arranged inside the protector and the spring is, at least partially, relaxed; and means for unlocking the spring.

The invention relates in particular to the field of single-use pre-filled injection syringes which are intended in particular for intramuscular or subcutaneous injections.

These devices are intended to limit to the greatest possible extent the risk, to the user, of accidental pricks after the injection since, once the contents of the syringe have been injected, the needle of the syringe is withdrawn from the patient and the protector is brought into the deployed position all around the needle.

In order to ensure a higher level of safety of use, it has been proposed to provide these devices with resilient means for displacing the protector around the needle of the syringe. In this manner, document U.S. Pat. No. 5,591,138 describes a device of the above-mentioned type which can be used in one of the two following manners: once the injection has been carried out with one hand, the user operates the unlocking means with his other hand in order to disengage the compression spring and to allow the deployment of the protector around the needle. Alternatively, the needle is introduced to a sufficient depth into the skin of the patient to bring about the unlocking of the spring, the spring not being able in any case to relax owing to the protector being pressed against the skin of the patient; in this case, the spring relaxes when the assembly of the device is moved away from the patient.

Therefore, this type of device requires, in order to achieve the desired deployment of the protector, either manipulation with two hands or the protector to be pressed against the skin of the patient. This manipulation ensures neither a high level of ease of use for the practitioner, nor great comfort for the patient. Therefore, these devices remain little used because their use is too far removed from the conventional use of an injection syringe. Furthermore, once the spring is unlocked, the decompression energy of the spring is often violently released without any control by the user being possible, which brings about a degree of instability of the device in the hand of the user. Furthermore, the rigid locking of the protector in the deployed position, in particular in order to prevent any re-use of the device, is possible only by the device being manipulated with two hands.

SUMMARY OF THE INVENTION

The object of the present invention is to provide a protection device which allows the protector to be deployed with the same hand as that which holds the syringe, with a simple releasing action without the protector needing to be pressed against the patient, and control of the displacement of the protector by the user being possible.

To this end, the invention relates to a protection device of the above-defined type for which the spring has, in the locked state, a predetermined force which is greater than the pushing effort necessary for displacing the syringe piston over substantially the entire injection path, and the unlocking means comprise a finger support flange which is fixedly joined to the protector and which is suitable for, on the one hand, transmitting to the spring a compression force less than that predetermined force when the piston slides for the injection and, on the other hand, transmitting to the spring a compression force greater than that predetermined force when the piston is at the end of the injection path.

According to other features of this device, taken in isolation or according to all technically possible combinations:

- the pushing effort is at least equal to the sum of the injection effort and the efforts for detaching and sliding the piston inside the body of the syringe;
- the flange is located at the proximal end of the protector;
- the length of the protector is substantially equal to that of the body of the syringe;
- for a syringe whose body is integrally provided with a neck at the proximal end thereof, the means for fixedly joining the protector support to the body of the syringe comprise means for fixing the support to the neck of the syringe,
- the fixing means comprise at least one clip-fit hook for the neck of the syringe;
- the support and the protector are arranged for rotation relative to each other between the retracted position of the protector and a position for unlocking the spring;
- the unlocking means comprise, on the one hand, at least a first groove which is arranged in one of the support or the protector, and which is at least partially inclined relative to the axial direction of the body of the syringe and, on the other hand, at least one pin which is fixedly joined to the other of the support or the protector and which is received in that first groove, the groove and the pin co-operating in order to guide in rotation the support and the protector relative to each other between the retracted position of the protector and the position for unlocking the spring;
- at least a second groove for receiving the pin, which groove communicates with the first groove, is arranged in the one of the support or the protector in which the first groove is arranged, the second groove extending substantially in the axial direction of the body of the syringe so as to be able to guide the support and the protector in translation relative to each other between the position for unlocking the spring and the deployed position of the protector;
- the distal base of the second groove forms an axial locking stop in the direction of deployment of the protector for the associated pin;
- it comprises means for locking the protector in the deployed position;
- those locking means comprise, on the one hand, at least one tongue which is fixedly joined to the support and, on the other hand, at least one deformable hook which is fixedly joined to the protector, each tongue and each hook respectively having two substantially conjugate contact surfaces which are suitable for radially deforming the corresponding hook when the support and the protector move from the retracted position to the deployed position of the protector, and each tongue and each hook respectively have two substantially conjugate axial stop surfaces which are suitable for locking the support and the protector relative to each other in the deployed position of the protector;

it comprises means for controlling the first use of the device; and those control means comprise, on the one hand, a detachable cap for being arranged around the needle of the syringe before use and, on the other hand, deformable tongues which are arranged at the distal end of the protector and which delimit a passage opening, the diameter of which is, when the tongues are not deformed, less than the maximum diameter of the cap.

The invention further relates to an injection device comprising, on the one hand, a syringe which comprises a needle, a tubular body, to the distal end of which the needle is fixed, and an injection piston which is slidingly arranged in the body and, on the other hand, a needle protection device which simultaneously comprises a needle protector which is substantially coaxial with the body of the syringe, a protector support which is fixedly joined to the body or which is provided with means for being fixedly joined to the body of the syringe, a spring which is arranged between and in contact with the support and the protector, the support and the protector being movable relative to each other between a retracted position of the protector, in which the needle of the syringe is disengaged and the spring is locked in a compressed state, and a deployed position, in which the needle is arranged inside the protector and the spring is, at least partially, relaxed, and means for unlocking the spring, wherein the needle protection device is as defined above.

BRIEF DESCRIPTION OF THE DRAWINGS

The invention will be better understood from a reading of the description below which is given purely by way of example and with reference to the drawings, in which.

DETAILED DESCRIPTION OF THE INVENTION

Figure 1:
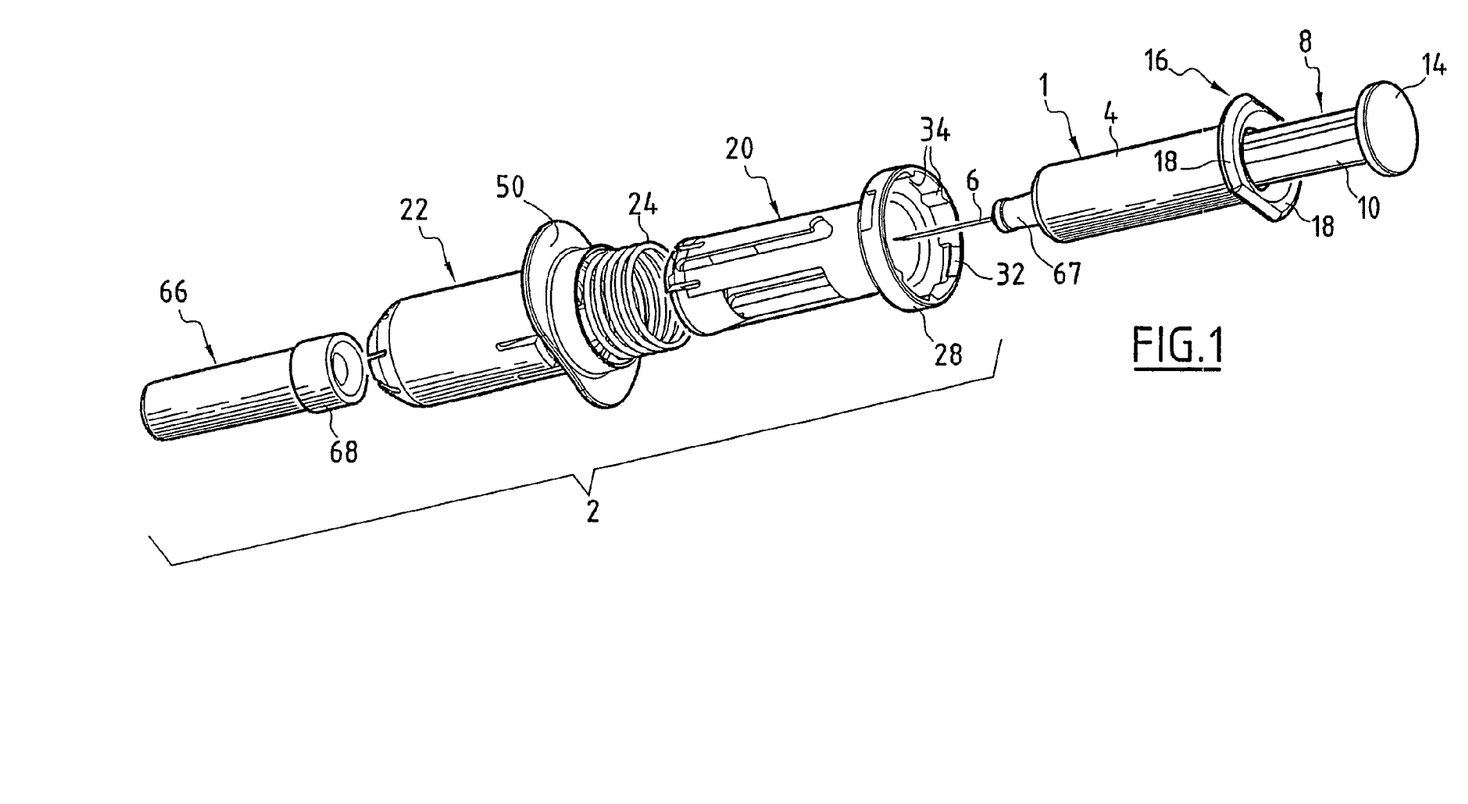
FIG. 1 is an exploded perspective view of an injection device according to the invention before assembly.

FIG. 1 is a perspective view of a syringe 1 and a protection assembly 2. Hereinafter, the terms "proximal" and "rear" are synonyms, as are the terms "distal" and "front".

The syringe 1 is a glass syringe of standard type, which is intended for single use. It contains a liquid to be injected into a patient in an intramuscular or subcutaneous manner. For this purpose, it comprises a body 4, a needle 6 which is fixedly joined to the distal end of the body 4 and a piston 8. This piston conventionally comprises a rod 10 which is provided, at the distal end thereof, with a push-button 12, which is not visible in FIG. 1, and a contact head 14, on which the thumb of the hand of the practitioner is intended to press.

The body 4 of the syringe comprises, in the proximal portion thereof, a neck 16 which circumferentially delimits two diametrically opposed lugs 18 which are generally intended, in particular in the absence of the assembly 2, to form contact surfaces for the index finger and second finger of the practitioner during the manipulation of the syringe and the injection of the liquid therein.

The protection assembly 2 generally having an axis X-X substantially comprises, as illustrated in FIG. 1:

a support 20 of generally tubular shape;

a protective sleeve 22 which is arranged coaxially relative to the support 20 and which has a diameter greater than that of the support, and a spring 24.

These three elements will be described in detail in succession below with reference to FIGS. 2 to 4.

The support 20 comprises a main portion 26 which is substantially cylindrical and which has an inside diameter substantially equal to the outside diameter of the body 4 of the syringe 1. This portion 26 continues at the proximal end thereof with a secondary portion 28 having larger inside and outside diameters than those of the main portion 26, a radial shoulder 29 being formed.

The proximal portion 28 is provided with means 30 for fixing to the syringe neck 16. In greater detail, these means 30 comprise, on the one hand, a pair of diametrically opposed deformable hooks 32 which are also visible in FIG. 1. Each of these hooks has a substantially frustoconical inclined surface 32A which widens towards the free end of the portion 28 and which is intended to be resiliently repelled by the lugs 18 of the syringe neck 16 when the support 20 is fixed to the syringe 1. The hooks 32 are remote from the shoulder 29 by a distance substantially equal to the thickness of the lugs 18. The hooks 32 thus form a clip-fit means for the syringe neck 16.

The fixing means 30 comprise, on the other hand, protrusions 34 (FIGS. 1, 4 and 6B) which project radially towards the interior of the portion 28. These protrusions are suitable for forming, on the one hand, angular indexing means, at approximately 180°, of the neck 16 of the syringe and, on the other hand, rotation locking stops for the neck 16 when the neck 16 is axially retained between the hooks 32 and the shoulder 29.

Two traversing grooves 36 are arranged facing each other in the main portion 26. Each groove is constituted by a first rectilinear portion 38, which extends substantially along axis X-X of the support 20 over a length greater than that of the needle 6, and a second rectilinear portion 40 which extends in an inclined manner relative to the same axis X-X. The inclined portion 40 opens at the proximal end portion of the main groove portion 38 and forms a V-shape, the point of which is directed towards the proximal side of the assembly 2.

Figures 2, 3, 4, 5:
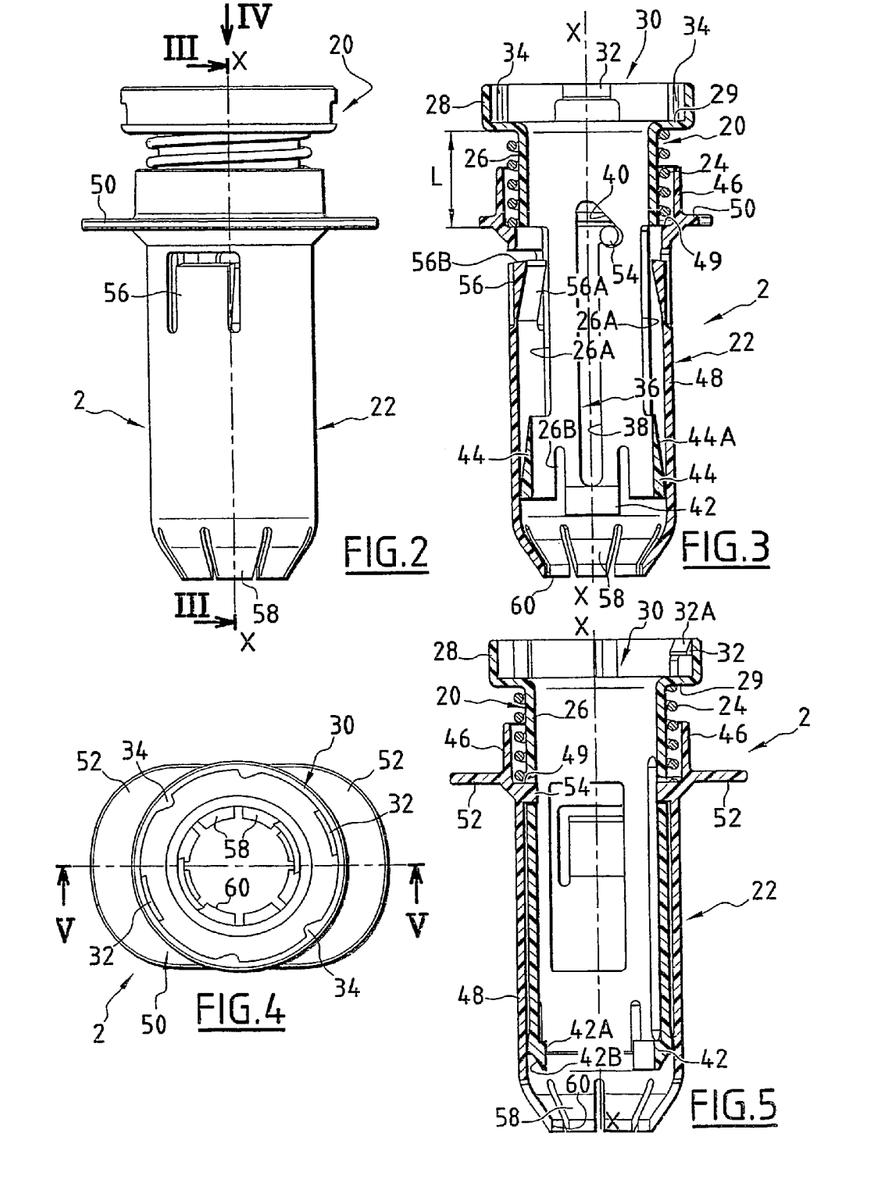
FIG. 2 is a front view of the protection device belonging to the injection device of FIG. 1 in the retracted position.
FIG. 3 is a sectioned view in plane III-III indicated in FIG. 2.
FIG. 4 is a top view according to arrow IV indicated in FIG. 2.
FIG. 5 is a sectioned view in the plane designated V-V in FIG. 4.

The main portion 24 comprises, at the distal end thereof, a first pair of diametrically opposed tongues 42 which are each located in the continuation of the grooves 36 (FIG. 5). These tongues 42 have an inner face 42A of substantially cylindrical shape and a substantially frustoconical outer face 42B which is divergent towards the rear.

The main portion 24 comprises a second pair of diametrically opposed tongues 44 which are located between the tongues 42 along the circumference of the distal end of this portion. They have a substantially frustoconical outer surface 44A, which is divergent towards the front, and a substantially planar distal surface 44B.

Plumb with these tongues 44 at the proximal end, longitudinal recesses 26A are arranged in the main portion 26 (FIG. 3).

In addition, at one side and the other of the tongues 42, axial slots 26B are provided starting from the distal end of the support in such a manner that, before the body 4 of the syringe 1 is inserted inside the support 20, these tongues 42 can be deformed radially, in particular inwards.

The protective sleeve 22 has a length substantially equal to that of the body 4 of the syringe 1. It is constituted by two cylindrical portions 46 and 48, the proximal portion 46 having a diameter slightly greater than that of the main portion 48. These two portions fit together to form a radial shoulder 49.

The sleeve 22 integrally comprises, in the proximal portion thereof, an external flange 50 in the form of two diametrically opposed lugs 52 (FIG. 4).

Two diametrically opposed studs 54 are fixedly joined to the sleeve (FIG. 5) also in the proximal portion of, but inside, the protective sleeve 22. These two studs are suitable for being received and guided in the two respective grooves 36 of the support 20, the support and the sleeve thus being movable relative to each other in translation along the common axis thereof and with limited rotation about the same axis when the pins 54 are located in the groove portions 40.

Figure 11:
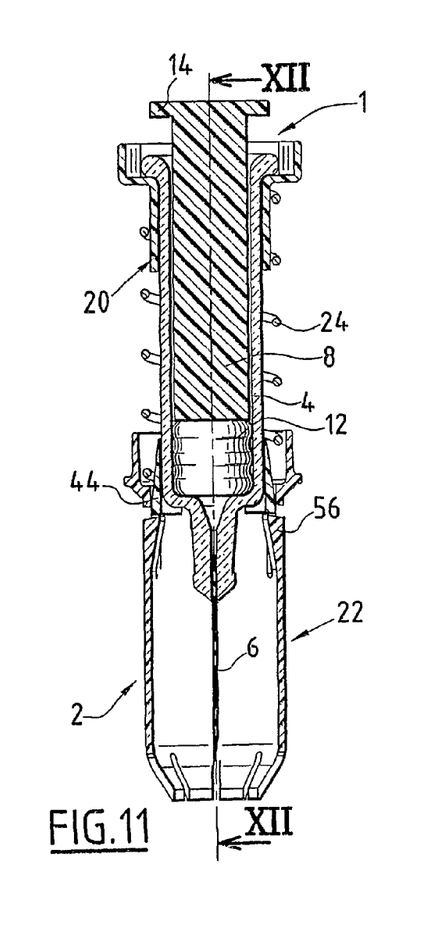
FIGS. 11 to 13 illustrate the injection device in the deployed position, FIG. 11 being a view similar to that of FIG. 8, FIG. 12 being a sectioned view in plane XII-XII indicated in FIG. 11 and FIG. 13 being a view identical to that of FIG. 11, the syringe not being illustrated.
Figure 12:
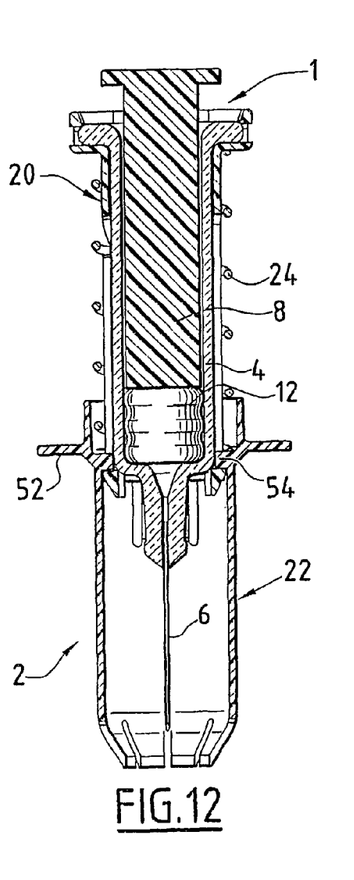
Figure 13:
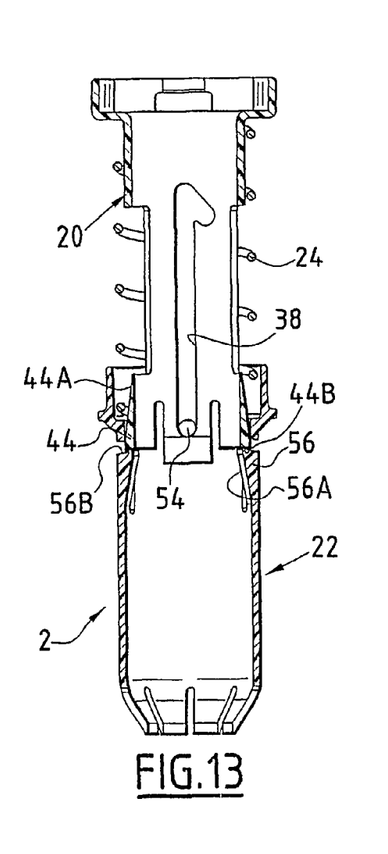

In greater detail, the support 20 and the sleeve 22 can be moved between a retracted position of the sleeve, in which the greater part of the sleeve covers the greater part of the support and the studs 54 are located at the distal end of each of the inclined groove portions 40, as illustrated in FIGS. 2 to 7, and a deployed position of the sleeve, in which the sleeve projects axially from the support and the studs are located at the distal end of the longitudinal groove portion 38, as illustrated in FIGS. 11 to 13.

When the syringe 1 is fixed to the assembly 2, these extreme positions correspond to an injection configuration, in which the needle 6 of the syringe 1 is disengaged and intended to be inserted into a patient, and a protection configuration, in which this needle is surrounded by the protective sleeve 22, respectively.

The proximal portion of the sleeve 22 further comprises internally a pair of diametrically opposed deformable hooks 56. Each of these hooks has, on the one hand, an inner surface 56A of substantially frustoconical shape which is divergent towards the front and which is complementary to that of the inner surfaces 44A of the tongues 44 of the support 20, and a proximal surface 56B which is substantially planar (FIG. 3).

In the retracted position of the sleeve, those hooks 56 extend inside the recesses 26A which are arranged in the support 20. In the deployed position of the sleeve, as illustrated in FIG. 11, the faces 56B of the hooks 56 are stopped axially against the tongues 44, the hooks and tongues in this manner forming a rigidly locking assembly in the deployed position.

The sleeve 22 is further provided at the distal end thereof with a crown of deformable tongues 58, the distal edges of which form a substantially circular opening 60 having a diameter less than the inside diameter of the main portion 26 of the support 20.

The spring 24 is a helical spring which is arranged between the protective sleeve 22 and the protector support 20. In greater detail, the spring is received between the shoulder 29 of the support 20 and the shoulder 49 of the sleeve 22. In the retracted position of the sleeve, the spring 24 is in a compressed state, thus having decompression energy linked to the tension of the spring and the difference between the length of the spring in the rest state and its length, designated L in FIGS. 2 to 7, in the compressed state. That is to say that the spring 24 has a predetermined supplementary compression force threshold which corresponds to the minimum force necessary to further compress the spring from the initial compressed state thereof of FIGS. 2 to 7. The tension of the spring and/or initial compression length L are selected so that this predetermined force threshold is greater than the pushing effort necessary to displace the piston 8 of the syringe 1 over the entire injection path thereof. In greater detail, the predetermined force of the spring in the locked state is greater than the sum of the injection effort, that is to say, the effort for evacuating the liquid out of the needle 6 of the syringe 1, and the efforts for detaching and sliding the push-button 12 inside the body 4 of the syringe.

Figure 6A:
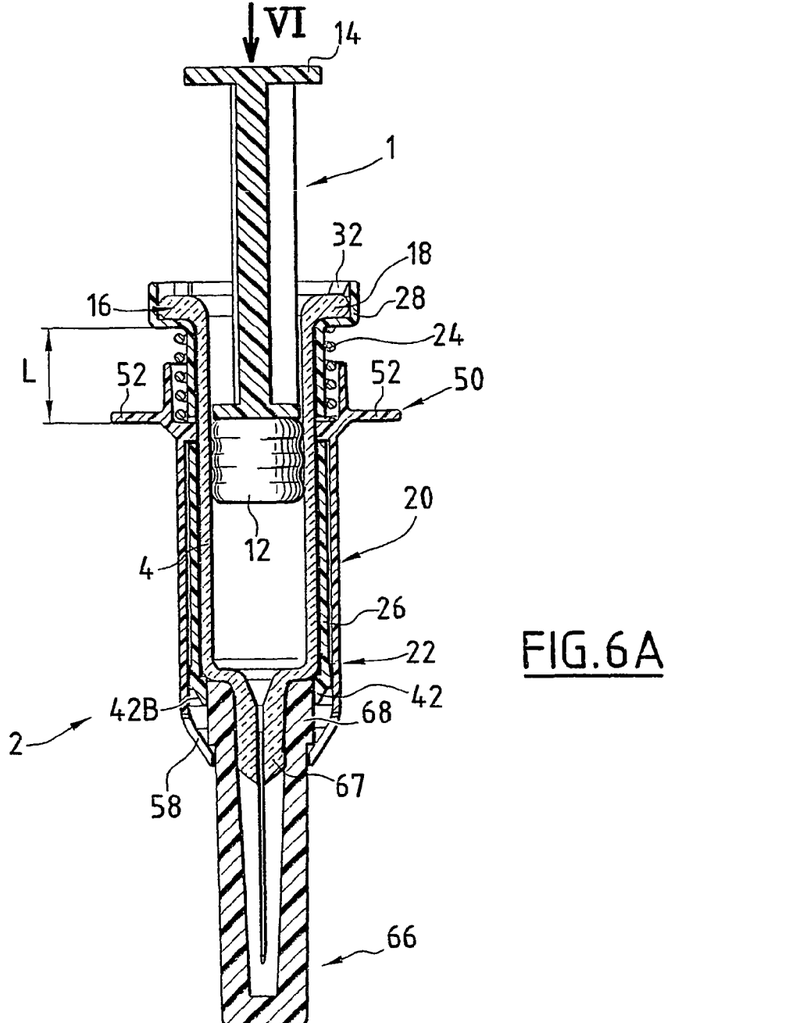
FIG. 6A is a view, in the same plane of section as that of FIG. 5, of the injection device according to the invention before use.

Optionally, the protection assembly 2 further comprises a cap 66 of generally tubular shape illustrated in FIGS. 1 and 6A.

The cap 66 is suitable for surrounding the needle 6 before the syringe 1 is used. This cap is closed at one of the ends thereof and the opposite end thereof is formed by an annular ring 68 having an outside diameter suitable both for being conjugate with the surface 42A of the hooks 42 of the support 20 and for being greater than the diameter of the opening 60 formed by the tongues 58 of the protective sleeve 22. The inner face of this ring 68 is intended to be adhesively bonded to the glass base 67 of the syringe body 4, where the needle 6 is fixed, in particular to ensure given sealing with respect to bacteria.

The operation of the injection device according to the invention is as follows:

Firstly, the protection device 2 is assembled in the retracted configuration, that is to say, that of FIGS. 2 to 7. The protective sleeve 22 is fitted around the support 20 for this purpose, starting from the distal end of the support, with the spring 24 being arranged between them. In greater detail, the sleeve is displaced axially backwards relative to the support, whilst at the same time radially deforming the hooks 56 outwards by means of a suitable tool, at least until the hooks 56 axially reach the front portion of the longitudinal recesses 26A. With the sleeve still being displaced backwards, the pins 54 are then pressed against the outer surfaces 42B of the tongues 42, with the tongues 42 being deformed inwards, until the pins are received in the groove portions 38. The displacement of the protector 22 backwards then continues until the pins 54 are received in the inclined groove portions 40, the support and the protector being pivoted relative to each other. The protector is thereby located in the retracted position.

Secondly, the glass syringe 1 is pre-filled with a liquid to be injected into a patient. This syringe is provided with the cap 66 which encloses the base 67 of the syringe body 4.

Figure 6B:
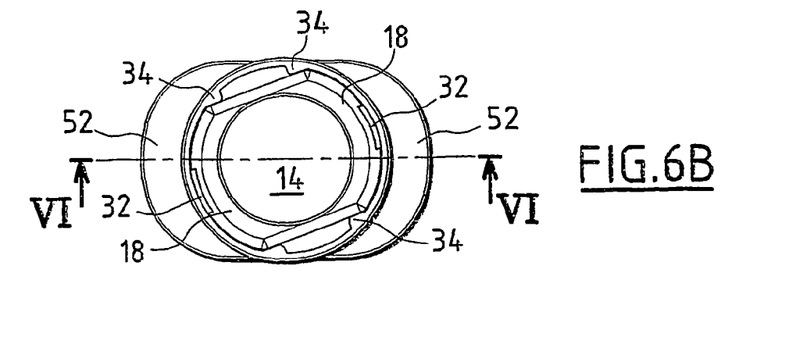
FIG. 6B is a top view according to arrow VI indicated in FIG. 6A.

The syringe and the cap are then inserted inside the assembly 2 in order to form the injection device, as illustrated in FIGS. 6A and 6B. In greater detail, the body 4 of the syringe is displaced substantially axially inside the support 20 until the syringe neck 16, which is indexed by the protrusions 34, clips inside the proximal portion 28, the hooks 32 being deformed radially outwards. The lugs 18 of the syringe neck 16 are then retained axially by the hooks 32, whilst the peripheral protrusions 34 retain the syringe neck, and therefore the syringe, in terms of rotation with respect to the support 20.

Furthermore, insofar as the syringe neck 16 is completely clipped inside the portion 28, it can no longer serve as usual to form a contact surface for the index finger and the second finger 9 of the practitioner. This support function is fulfilled by the flange 50 which is fixedly joined to the sleeve 22. Insofar as the length of the protective sleeve 22 is substantially equal to that of the syringe body 4 and/or the flange 50 is arranged in the region of the proximal end of this sleeve, the practitioner can manipulate the syringe by resting his thumb on the contact head 14 of the piston 8 as in the accustomed manner, and by resting his index finger and second finger on the faces of the lugs 52 that are directed towards the needle 6.

Furthermore, when the syringe 1 is fixed to the protector support 20, as illustrated in FIGS. 6A and 6B, the cap 66 projects outside the protective sleeve 22.

When the practitioner is ready to carry out the injection of the liquid contained in the syringe, he retracts the cap 66 by drawing it axially forwards. The ring 68 then passes through the opening 60, deforming the tongues 58. Once the cap 66 has been retracted, the tongues 58 again take up the initial position thereof. The passage hole 60 at the distal end of the sleeve, having a diameter smaller than the outside diameter of the cap 68, then prevents the cap from being repositioned around the needle. The co-operation of the cap 66 and the tongues 58 thus forms a control means for the first use of the injection device.

Figure 7:
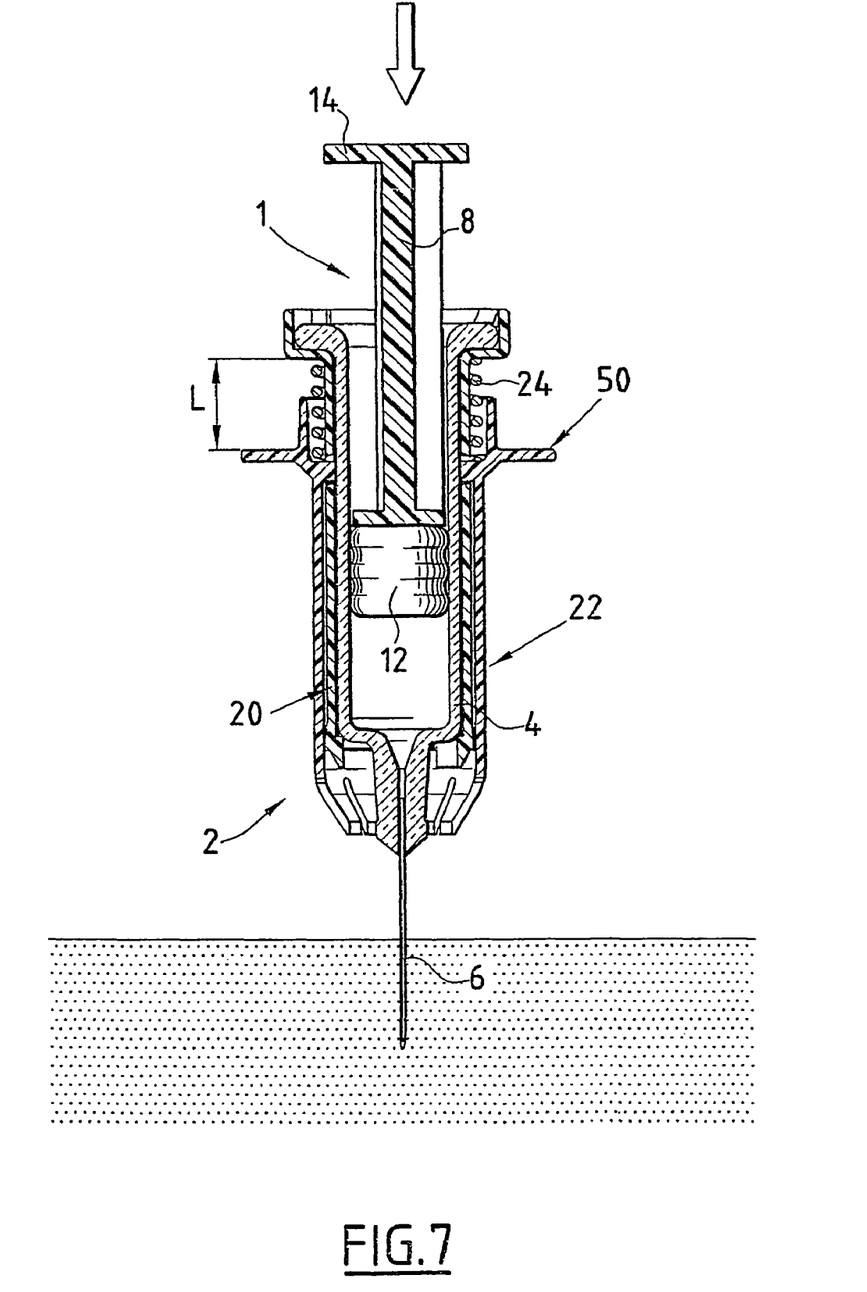
FIG. 7 is a view similar to that of FIG. 6A, the injection device being in use.

The practitioner then inserts the needle 6 into a patient. He injects the liquid contained in the syringe by applying a pushing action to the contact head 14 of the piston 8, his index finger and second finger remaining in contact with the faces of the lugs 52 that are directed towards the needle. During the injection, no movement is brought about between the protector support 20 and the protective sleeve 22, the spring 24 remaining compressed with a length L, as illustrated in FIG. 7.

The injection continues until the push-button 12 of the piston 8 reaches the end of the injection path.

Figure 8:
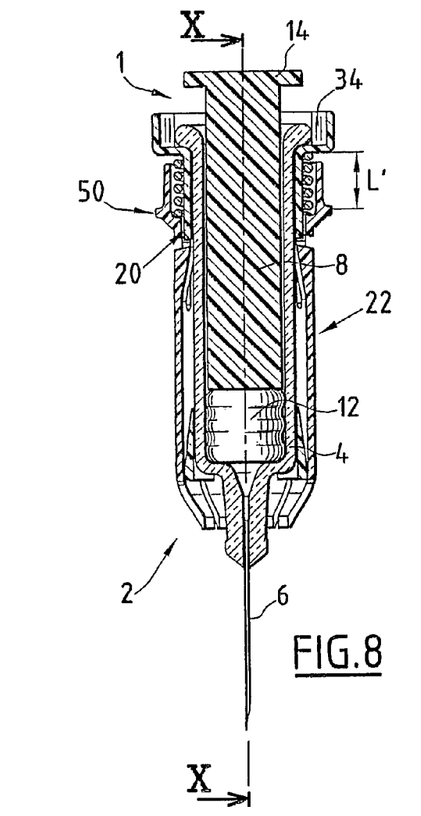
FIG. 8 is a view, in the same plane of section as that of FIG. 3, of the injection device after use.
Figure 9:
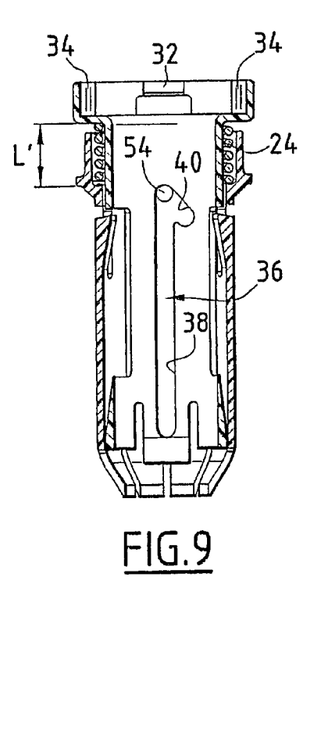
FIG. 9 is a view identical to that of FIG. 8, the syringe of the injection device not being illustrated.
Figure 10:
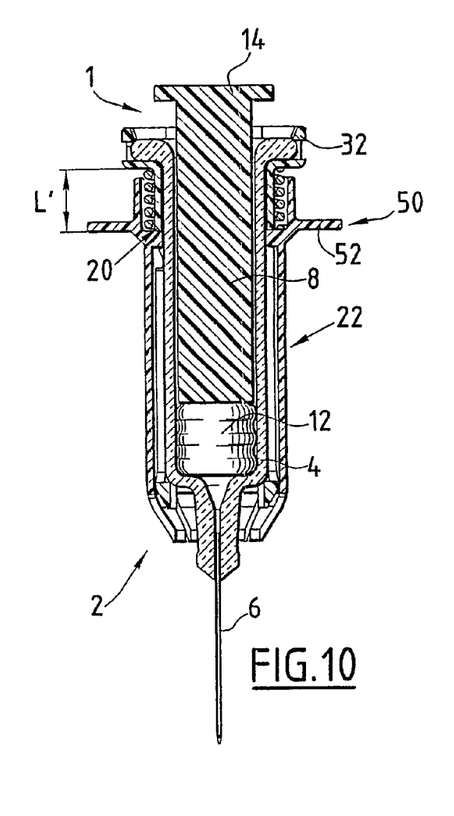
FIG. 10 is a sectioned view in plane X-X indicated in FIG. 8.

The practitioner then withdraws the needle from the patient. In order to release the protection assembly 2, the practitioner applies an additional pressure to the piston rod 8. This pressure must be greater than the predetermined force produced by the spring 24 in the locked state, so that this spring is further compressed and changes from the length L thereof to a smaller length L', as illustrated in FIGS. 8 to 10. To this end, considering the syringe support to be stationary, the protective sleeve 24 is displaced axially towards the proximal end of the support 20. The practitioner brings about this movement by applying a corresponding pressure by means of his index finger and his second finger to the lugs 52 of the flange 50 of the sleeve 22. This pressure brings about, in a manner combined with the translation movement, the rotation of the protective sleeve 22 about the syringe support 20, the studs 54 being guided by the inclined groove portions 40. This rotation movement continues until the studs reach the proximal end of this groove portion 40, that is to say, the proximal end of the longitudinal groove portion 38, as can be seen in FIG. 9. The device 2 is then in the unlocking position of the spring 24.

The practitioner then releases the pressure which he had been applying to the flange 50 until then, allowing the spring 24 to relax as far as a rest state. The pins 54 move in translation inside the longitudinal groove portion 38 as far as the distal end thereof, as illustrated in FIG. 13. The translation movement of the sleeve 22 relative to the support 20 can be controlled by the practitioner if he progressively releases the finger-hold which he applies to the flange 50. When the pins 54 have arrived at the distal end of the groove 36 (FIG. 13), the protector is in the deployed position thereof.

Furthermore, when the sleeve 22 is moving in translation relative to the support 20, the hooks 56 make use of the longitudinal recesses 26A of the support until they slide along the distal tongues 44 of the support 22 by co-operation between the complementary surfaces 56A and 44A thereof.

In the deployed position of the protector, the tongues 44 retain the hooks 56 in position by co-operation between the surfaces 56B and 44B so that the protective sleeve 22 cannot be moved into the initial position thereof. Similarly, the sleeve 44 cannot readily be detached from the support 20 because the pins 54 are stopped against the distal base of the longitudinal groove portion 38 (FIG. 13), the tongues 42 forming this base being radially retained between the body of the syringe 1 and the sleeve 22.

The injection device according to the invention is simple to use in this manner, whilst at the same time allowing the practitioner to control the movement for covering the needle with the protective sleeve. The number of components constituting the protection assembly 2 illustrated is reduced to three.

The device according to the invention can be adapted to various types of syringe, both in terms of the shapes and the volumes thereof. Therefore, this device has the advantage of not calling into question the general shape of the syringes used and consequently does not bring about any modification of the industrial methods for filling these syringes.

Various variants of the device according to the invention can be envisaged:

unlike the embodiment described above, the pins 54 and/or the flange 50 of the protective sleeve 22 can be separate from the sleeve 22 and not produced integrally therewith;

contrary to the device described, the studs 54 can be produced on the outer surface of the protector support 20 and the guiding groove 36 arranged in the protective sleeve 22;

the support 20 can be produced in one piece with the syringe body 4; and/or the protrusions 34 of the means 30 for fixing the support 20 to the syringe neck 16 can be dispensed with and optionally replaced with one or more hooks which are similar to the hooks 32 described above, the assembly of these hooks axially retaining the neck 16 relative to the support 20 for any relative angular position between the syringe 1 and the support; in this case, the syringe 1 is free to rotate inside the support 20 which, on the other hand, ensures greater ease of fixing the protection assembly 2 to the syringe (absence of indexing).

The invention claimed is:

1. A needle protection device for a syringe (1) which comprises a needle (6), a tubular body (4), to the distal end of which the needle (6) is fixed, and an injection piston (8) which is slidingly arranged in the body (4), this device comprising
   a needle protector (22) which is substantially coaxial with the body (4) of the syringe (1);
   a protector support (20) which is fixedly joined to the body (4) or which is provided with means (30) for being fixedly joined to the body (4),
      wherein a spring (24) which is arranged between and in contact with the support (20) and the protector (22), the support and the protector being movable relative to each other between a retracted position of the protector, in which the needle (6) of the syringe (1) is disengaged and the spring (24) is locked in a compressed state, and a deployed position, in which the needle is arranged inside the protector (22) and the spring is, at least partially, relaxed; and means for unlocking the spring (24), characterised in that the spring (24) has, in the locked state, a predetermined force which is greater than the pushing force necessary for displacing the piston (8) of the syringe (1) over substantially the entire injection path, and in that the unlocking means comprise a finger-supporting flange (50), which is adapted to support a finger of a user, which is fixedly joined to an external surface of the protector (22), the finger-supporting flange (50) being located external to the protector support (20), and which is for, on the one hand, transmitting to the spring (24) a compression force less than that predetermined force when the piston (8) slides for the injection and, on the other hand, further compressing the spring (24) with a compression force greater than that predetermined force when the piston (8) is at the end of the injection path.

2. Device according to claim 1, characterised in that the pushing force is at least equal to the sum of an injection force, for evacuating liquid out of the needle (6) of the syringe (1), and forces for detaching and sliding the piston (8) inside the body (4) of the syringe (1).

3. Device according to claim 1, characterised in that the flange (50) is located at the proximal end of the protector (22).

4. Device according to claim 1, characterised in that the length of the protector (22) is substantially equal to that of the body (4) of the syringe (1).

5. Device according to claim 1, characterised in that, for a syringe (1) whose body (4) is integrally provided with a neck (16) at the proximal end thereof, the means for fixedly joining the protector support (20) to the body (4) of the syringe (1) comprise means (30) for fixing the support to the neck (16) of the syringe (1).

6. Device according to claim 5 characterised in that the fixing means (30) comprise at least one clip-fit hook (32) for the neck (16) of the syringe (1).

7. Device according to claim 1, characterised in that the support (20) and the protector (22) are arranged for rotation relative to each other between the retracted position of the protector and a position for unlocking the spring (24).

8. Device according to claim 7, characterised in that the unlocking means comprise, on the one hand, at least a first groove (40) which is arranged in one of the support (20) or the protector (22) and which is at least partially inclined relative to the axial direction of the body (4) of the syringe (1) and, on the other hand, at least one pin (54) which is fixedly joined to the other of the support (20) or the protector (22) and which is received in that first groove (40), the groove and the pin co-operating in order to guide in rotation the support and the protector relative to each other between the retracted position of the protector and the position for unlocking the spring (24).

9. Device according to claim 8, characterised in that at least a second groove (38) for receiving the pin (54), which groove (38) communicates with the first groove (40), is arranged in the one of the support (20) or the protector (22) in which the first groove (40) is arranged, the second groove (38) extending substantially in the axial direction of the body (4) of the syringe (1) so as to be able to guide the support (20) and the protector (22) in translation relative to each other between the position for unlocking the spring (24) and the deployed position of the protector (22).

10. Device according to claim 9, characterised in that the distal base of the second groove (38) forms an axial locking stop in the direction of deployment of the protector (22) for the associated pin (54).

11. Device according to claim 1, characterised in that it comprises means (44, 56) for locking the protector (22) in the deployed position.

12. Device according to claim 11, characterised in that those locking means comprise, on the one hand, at least one tongue (44) which is fixedly joined to the support (20) and, on the other hand, at least one deformable hook (56) which is fixedly joined to the protector (22), in that each tongue (44) and each hook (56) respectively have two substantially conjugate contact surfaces which are suitable for radially deforming the corresponding hook (56) when the support (20) and the protector (22) move from the retracted position to the deployed position of the protector, and in that each tongue (44) and each hook (56) respectively have two substantially conjugate axial stop surfaces (44B, 56B) which are suitable for locking the support (20) and the protector (22) relative to each other in the deployed position of the protector.

13. Device according to claim 1, characterised in that it comprises means for controlling the first use of the device (20).

14. Device according to claim 13, characterised in that those control means comprise, on the one hand, a detachable cap (66) for being arranged around the needle (6) of the syringe (1) before use and, on the other hand, deformable tongues (58) which are arranged at the distal end of the protector (22) and which delimit a passage opening (60), the diameter of which is, when the tongues (58) are not deformed, less than the maximum diameter of the cap (66).

15. Injection device comprising, on the one hand, a syringe (1) which comprises a needle (6), a tubular body (4), to the distal end of which the needle (6) is fixed, and an injection piston (8) which is slidingly arranged in the body (4) and, on the other hand, a needle protection device (2) which comprises a needle protector (22) which is substantially coaxial with the body (4) of the syringe (1), a protector support (20) which is fixedly joined to the body (4) or which is provided with means (30) for being fixedly joined to the body (4), a spring (24) which is arranged in contact between the support (20) and the protector (22), the support and the protector being movable relative to each other between a retracted position of the protector, in which the needle (6) of the syringe (1) is disengaged and the spring (24) is locked in a compressed state, and a deployed position, in which the needle is arranged inside the protector (22) and the spring is, at least partially, relaxed, and means for unlocking the spring (24), characterised in that the needle protection device (2) is in accordance with claim 1.

16. The device according to claim 1, wherein the spring remains arranged between and in contact with the support and the protector in both the retracted and deployed positions.

17. The device according to claim 1, wherein, during an unlocking operation of the means for unlocking the spring, the protector moves toward a proximal end of the protector support prior to moving into the deployed position.

18. The device according to claim 1, wherein the means for unlocking the spring is not deformed during an unlocking operation.

19. The device according to claim 1, wherein a triggering force required to initiate an unlocking operation of the means for unlocking the spring is substantially determined by the predetermined force required to further compress the spring.

* * * * *